United States Patent [19]

Oh

[11] Patent Number: 5,046,611

[45] Date of Patent: Sep. 10, 1991

[54] HEMOSTATIC CLIP CARTRIDGE

[75] Inventor: Seik Oh, Raleigh, N.C.

[73] Assignee: Edward Weck Incorporated, Princeton, N.J.

[21] Appl. No.: 602,449

[22] Filed: Oct. 22, 1990

[51] Int. Cl.⁵ .................................... B65D 85/24
[52] U.S. Cl. .................................... 206/339
[58] Field of Search ................. 206/338–341

[56] References Cited

U.S. PATENT DOCUMENTS

| | | | |
|---|---|---|---|
| 4,294,355 | 10/1981 | Jewusiak et al. | 206/339 |
| 4,361,229 | 11/1982 | Mericle | 206/341 X |
| 4,696,396 | 9/1987 | Samuels | 206/339 |
| 4,936,447 | 6/1990 | Peiffer | 206/339 |
| 4,961,499 | 10/1990 | Kulp | 206/339 |
| 4,971,198 | 11/1990 | Mericle | 206/339 |
| 4,972,949 | 11/1990 | Peiffer | 206/339 |

Primary Examiner—William I. Price
Attorney, Agent, or Firm—Gene Warzecha

[57] ABSTRACT

A holder for retaining a plurality of hemostatic or ligating clips. The holder retains a single clip in each chamber and is intended to be used with a forceps-type clip applier, the jaws of which may be inserted into a desired chamber to retrieve a clip therefrom. Each individual chamber is formed of a pair of facing transverse walls and a central post which loosely supports a hemostatic clip. Each transverse wall has at least one resilient flap extending downwardly and inwardly in such a way that the bottommost portion of the resilient flap contact the side of the body of the clip in the chamber. The holder is ideally suited to retain plastic or polymer clips and may be made as an assembly of discrete components or in a single, molded integral form.

2 Claims, 4 Drawing Sheets

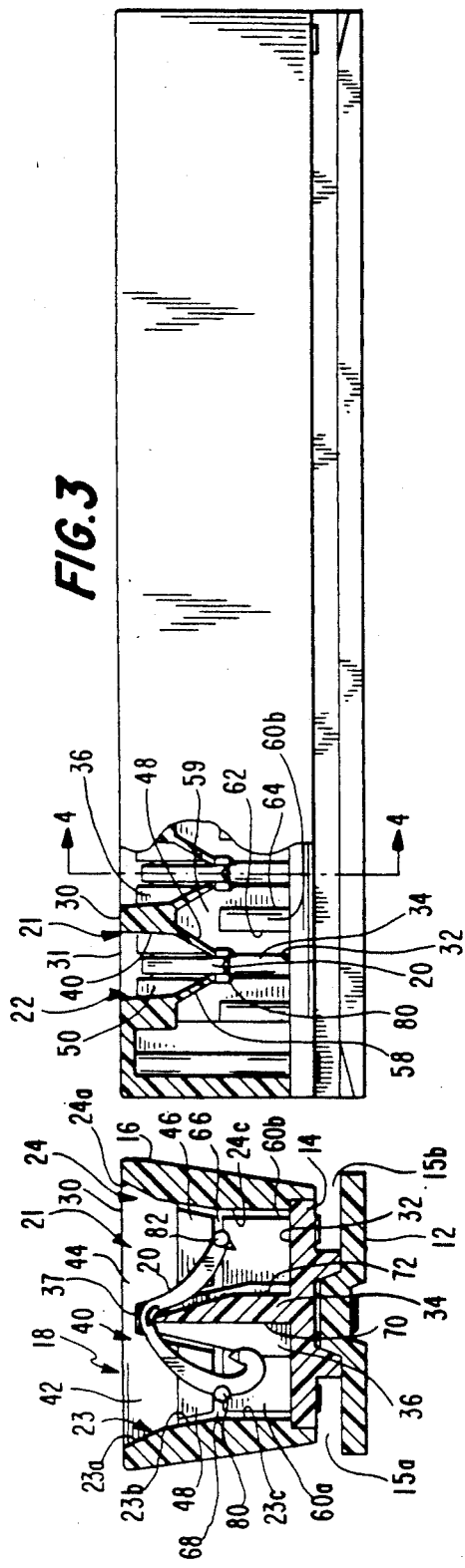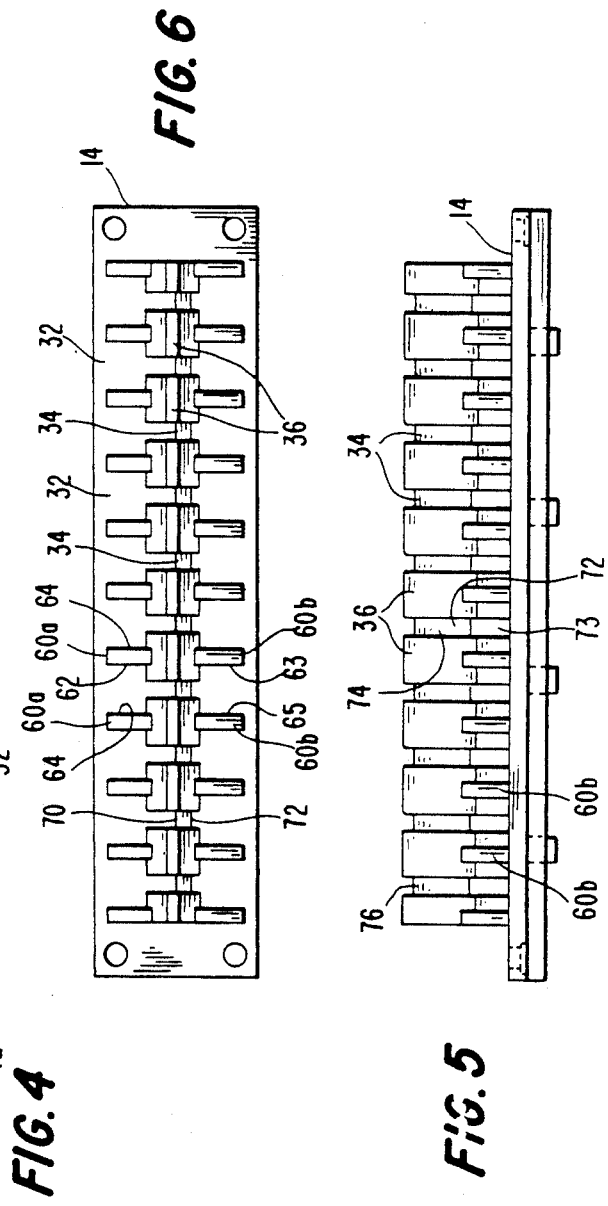

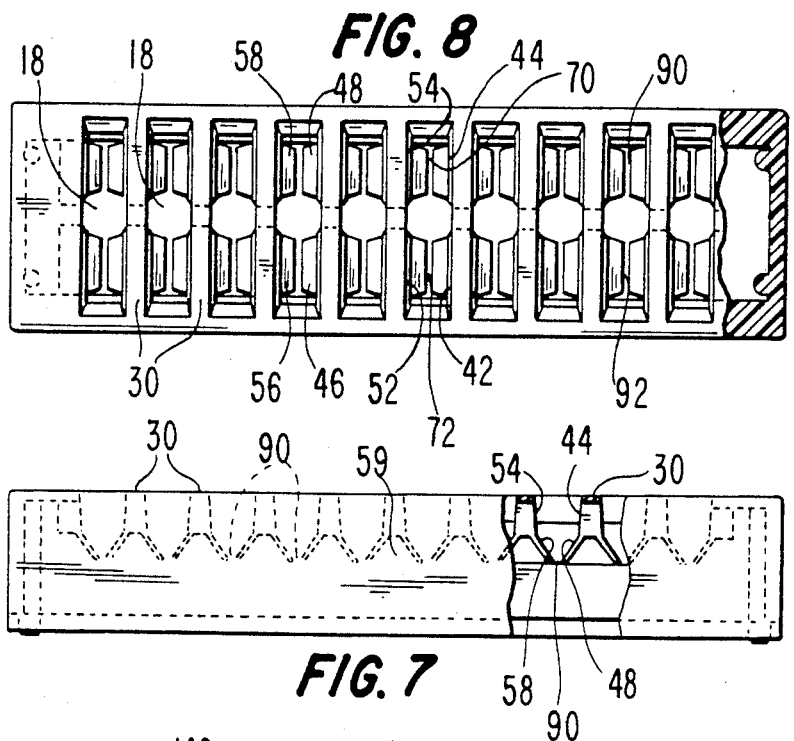

HEMOSTATIC CLIP CARTRIDGE

BACKGROUND OF THE INVENTION

1. Field of the Invention

The invention relates generally to holders for storing and retaining hemostatic clips prior to use. More particularly, the invention relates to hemostatic clip cartridges which facilitate the storage and retention of a plurality of hemostatic clips within a corresponding plurality of individual chambers of the cartridge prior to withdrawal of the clips by a forceps-type clip applier.

2. Description of the Prior Art

Hemostatic clips have long been used to ligate or clamp blood vessels during surgical procedures. The clips are generally made of either a biocompatible metallic material or of a polymeric or non-metallic material. The term "non-metallic" as used herein means anything other than metallic materials. In general, the clips are generally C-shaped, U-shaped or V-shaped and are designed such that the opposing legs of the open clip are able to be closed together by being compressed by the jaws of a forceps-type clip applier. In the case of metallic clips, the material is sufficiently strong such that the clips remain in their crimped, closed position merely by squeezing the legs together. In the case of plastic-type clips, the material is not as strong and requires some auxiliary latching mechanism to keep the clips closed. For the foregoing reasons, metallic clips are generally symmetrical while plastic clips are not. The latching mechanism generally comprises a hook-type arrangement molded with or otherwise secured to the plastic clip. One example of such a plastic ligating clip is shown in U.S. Pat. No. 4,834,096 (Oh et al.) assigned to the assignee hereof.

Because the clips are small and because many clips are usually used in a surgical procedure, holding devices are used to store and retain the clips—whether metallic or plastic—between the time of their manufacture and ultimate use in a surgical procedure. While numerous clip cartridges are known, they all serve to prevent the clips from becoming loosened during shipment and handling and from becoming completely dislodged. A distinction should be made between clip cartridges intended for use with "manual" clip appliers and those intended for use with "automatic" clip appliers. As used herein, the term "automatic" means those clip appliers which retain a plurality of hemostatic clips adjacent the jaws of a clip applier in a way such that a new clip is automatically fed to the jaws after the previous clip has been crimped into place. As used herein, the term "manual" means clip appliers which receive one clip at a time between the jaws and which have to be reloaded manually after the previous clip is crimped. The reloading operation is generally accomplished by inserting the jaws of the applier into a clip holder or cartridge which is generally provided with a plurality of longitudinally spaced, clip retaining chambers. A single clip is retained in each chamber by a variety of means and removed from its chamber by a forceps-type clip applier which is inserted as desired into each clip chamber and secured to the clip sufficiently to overcome whatever clip retention means is utilized to enable the clip to be removed from the clip chamber.

Various mechanisms are known by which clips may be retained within the chambers of clip cartridges. With respect to metallic clips, friction between the clip and the side walls of its individual chamber is generally sufficient to retain the clip. The clip cartridges are generally made of molded plastic material such that the walls of each clip chamber are somewhat resilient and able to be pushed away from each other when the clip applier jaws are inserted into the chamber to retrieve the clip. An example of a cartridge holding the clips in their respective clip chambers by means of frictional engagement with the side walls of each chamber is shown in U.S. Pat. No. 4,076,120 (Carroll et al.). In some prior art clip cartridges, each individual clip chamber is provided with a central post generally conforming to the shape of the open clip although being slightly larger so that when the clip is pushed onto the central post, frictional contact between the legs of the clip and the central post retains the clip within its chamber. Cartridges of this type are shown in U.S. Pat. Nos. 3,270,745, 3,326,216, 3,363,628, 3,439,522 and 3,439,523, all issued to E.C. Wood.

Prior art cartridges are also known which retain clips in a partially straightened state by maintaining each clip under tension within its chamber by the interaction between the central post in the chamber and the central part of the clip and protrusions extending into each chamber toward the central post (from the ends). The clip is retained by having its central hinge part pushed upwardly by the central post and its ends pushed downwardly by the protrusions. Such a cartridge is shown in U.S. Pat. No. 3,713,533 (Reimels) and U.S. Pat. No. 4,146,130 (Samuels et al.)

Another type of prior art cartridge is known which has a plurality of ribs extending from each side wall of each clip chamber inwardly toward the clip to retain the clip by frictional engagement with the ribs (U.S. Pat. No. 4,696,396, Samuels). The aforementioned U.S. Pat. No. 4,146,130 (Samuels et al.) shows an alternative embodiment for the situation where clips are intended to be loosely maintained in the cartridge without frictional engagement between it and the chamber, the clips in such an event being retained in each cartridge by a covering tape which may be easily severed by the applier as desired.

With respect to non-metallic clips, the prior art cartridges suitable for holding metallic clips are not necessarily suitable because the plastic clips inherently have a greater resiliency and non-symmetrical structure. For example, the aforementioned prior art cartridges which rely on the interaction between the clip and central post are not suitable for use with non-metallic clips because there is generally insufficient compression in non-metallic clips to cause them to g rip the center post adequately. Likewise, frictional engagement with either the side and/or end walls of the chamber could possibly, over a long period of storage time, adversely affect performance of the clips. It would be preferable to retain non-metallic clips in a natural, relaxed state without any external stress applied to the clips until they are ready for use.

One known prior art method of holding plastic clips is shown in U.S. Pat. No. 4,294,355 (Jewusiak et al.) which discloses one or more resilient fingers associated with each clip chamber for holding each clip in a particular fixed orientation. The entire cartridge may or may not be covered by a thin film having a plurality of lines of weakness over each clip to identify the clip location for easy retrieval by the clip applier.

U.S. Pat. No. 4,361,229 (Mericle) discloses a cartridge for non-metallic clips wherein each clip is retained in its individual chamber by the interaction between a central post supporting each clip and paper flaps extending into each end of each chamber, the paper flaps being formed from a paper film interposed between a base portion of the cartridge (to which the central post is secured) and a top portion.

The known prior art cartridges suitable for plastic clips are relatively complex to manufacture and load and it is an object of this invention to produce a hemostatic clip holder of simplified structure and which also simplifies the loading of clips into the holder It is another object of this invention to provide a hemostatic clip holder for retaining clips during shipping and handling while enabling the withdrawal of the clips by clip appliers in preparation for use.

It is also an object of this invention to produce a unitary clip holder for storing and retaining a plurality of hemostatic clips for subsequent removal by an associated clip applier.

It is a further object of this invention to produce a hemostatic clip holder for storing and retaining a plastic hemostatic clip for subsequent removal by an associated clip applier.

It is a further object of this invention to produce a hemostatic clip cartridge for storing and retaining a plurality of plastic hemostatic clips in a natural, relaxed state prior to their subsequent removal by an associated clip applier.

SUMMARY OF THE INVENTION

These and other objects of this invention are achieved by the preferred embodiment of the invention disclosed herein which is embodied in a cartridge for holding hemostatic clips comprising an elongated body provided with a plurality of longitudinally spaced chambers, each chamber for receiving a hemostatic clip. Each chamber is separated from its adjacent chamber by a transverse wall extending across the body, each transverse wall having a downwardly extending wall surface and an integrally formed resilient flap downwardly and inwardly extending from the bottommost end of the wall surface. Each chamber is provided with a central post which supports an open hemostatic clip while it is also retained in the chamber by the slight pressure of the resilient flaps.

BRIEF DESCRIPTION OF THE DRAWINGS

FIG. 3 shows a side elevational view of FIG. 1 partly in cross-section.

FIG. 4 is a cross-sectional view of FIG. 3, taken along the lines 4-4.

FIG. 5 is a side elevational view of portion of FIG. 2.

FIG. 6 is a top plan view of FIG. 5.

FIG. 7 is a side elevational view of another portion of FIG. 2, partly in cross-section.

FIG. 8 is a top plan view of FIG. 7 partly in cross-section.

FIG. 9 is a perspective view of an alternate embodiment of the clip cartridge of FIG. 1.

FIG. 10 is a side elevational view of the embodiment of FIG. 9 showing a clip in one chamber.

FIG. 11 is a cross-sectional view of FIG. 10 taken along lines 11-11.

DESCRIPTION OF THE PREFERRED EMBODIMENT

Figure 1:
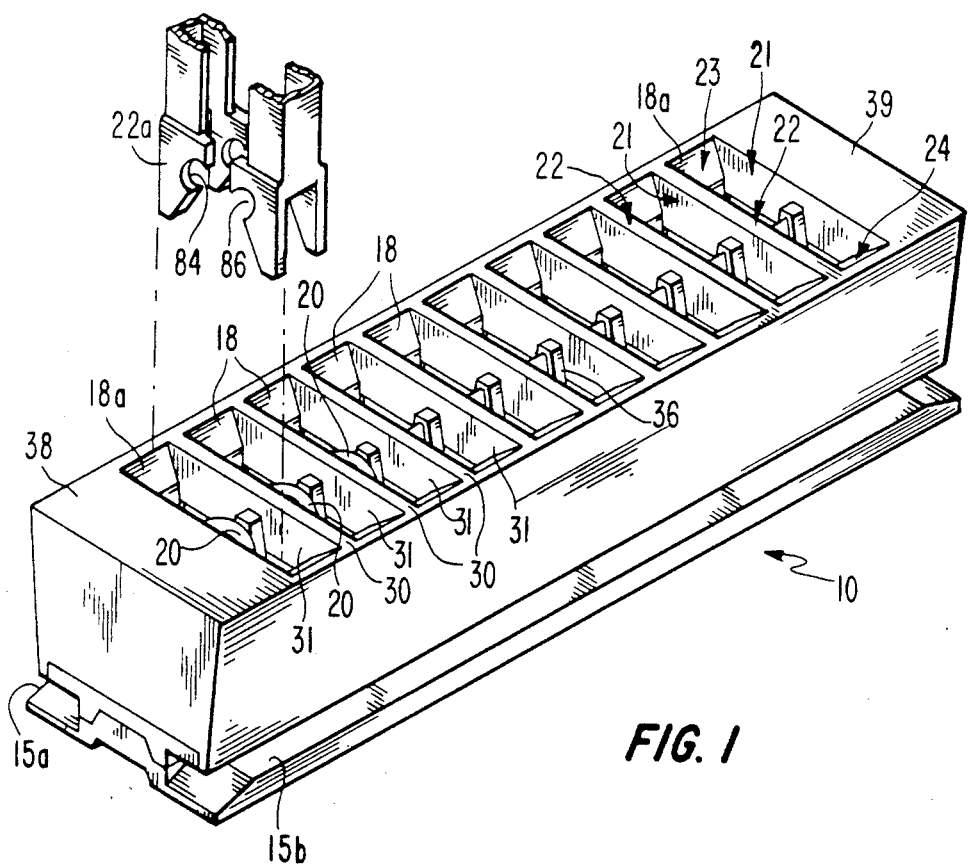
FIG. 1 shows a front perspective view of a clip cartridge constructed in accordance with the principles of this invention and a portion of a clip applier for use with the clips retained by the cartridge.
Figure 2:
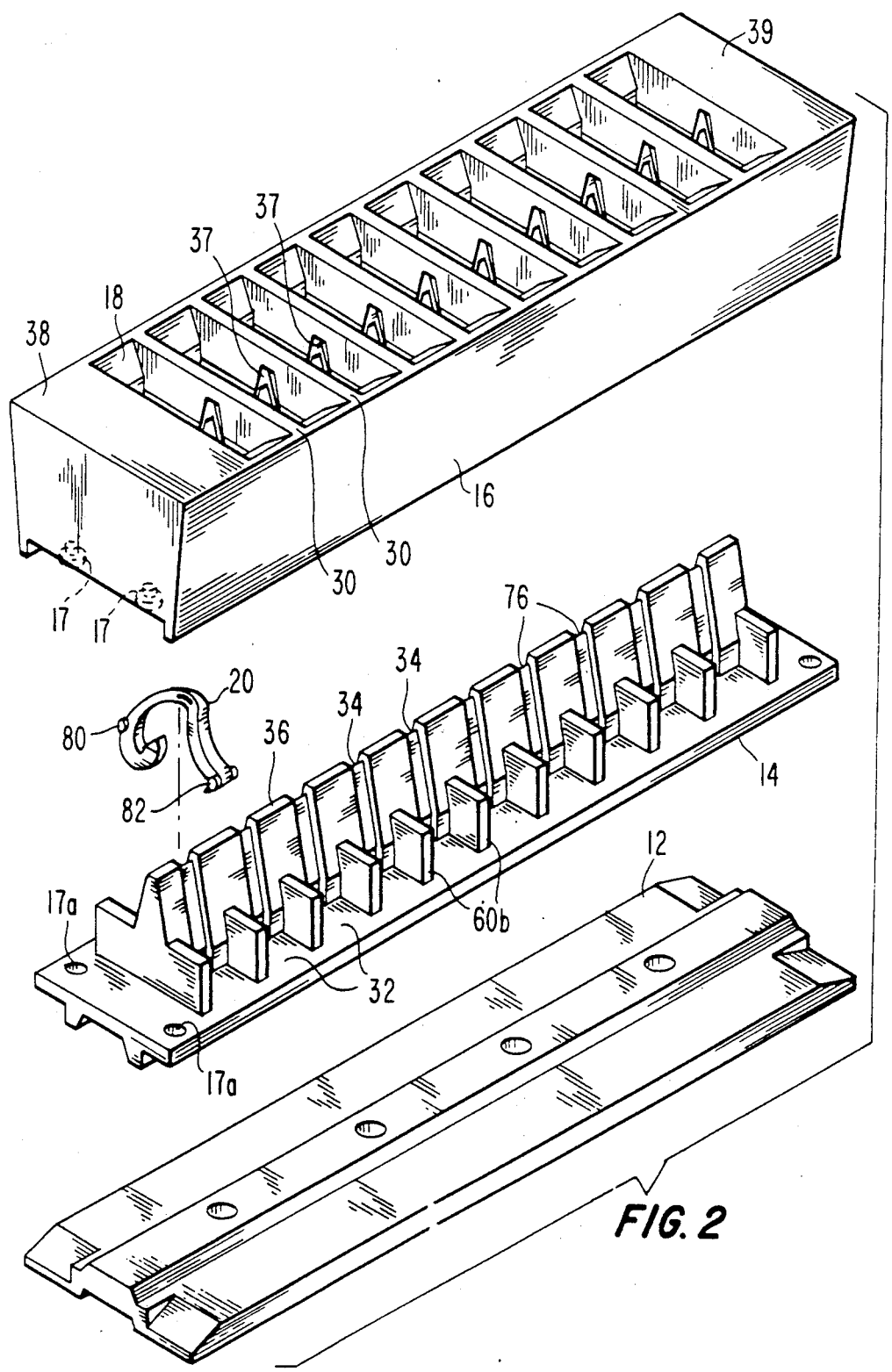
FIG. 2 shows an exploded view of the cartridge of FIG. 1 showing the components thereof.

Referring first to FIG. 1, there is shown a perspective view of a clip cartridge 10 constructed in accordance with the principles of this invention. As best seen in FIG. 2, clip cartridge 10 may be an assembly of a base element 12, post element 14 and cover 16, the various components being secured together by conventional snap-fit posts 17 (mateable with apertures 17a), ultrasonic welding, etc. In the embodiment shown in FIGS. 1 and 2 the elements 12, 14 and 16 are each independently integrally molded. However, it will be understood that alternative embodiments may have base element 12 and post element 14 integrally formed together (not shown) or the entire assembly may be integrally formed as shown in the alternate embodiment depicted in FIGS. 9-11.

When assembled, base element 12 is spaced from post element 14 in order to produce a pair of parallel channels 15a and 15b which serve to facilitate securing the cartridge to a tray or other component during use. Cover 16 is a longitudinally extending hollow body (best seen in FIG. 7) having an open bottom, a slotted top wall and side and end walls which, when secured to post element 14 produces the body of clip cartridge 10 which comprises a plurality of individual clip retaining chambers or compartments 18 (the end chambers being labelled 18a), each of which is identical and retains a clip 20. In FIG. 1, only some of the chambers 18 are shown with a clip 20, the remaining ones being empty, and a representative clip applier 22a is diagrammatically shown in position over one of the clip chambers 18. It should be understood that virtually any clip applier will be suitable for use with cartridge 10 provided it is operable with the particular clip loaded into the cartridge. In the drawings, the clip and representative applier are those disclosed in U.S. Pat. No. 4,834,096 (Oh et al.), assigned to the assignee hereof and incorporated by reference herein.

Each clip chamber 18 is formed by the cooperative action of cover 16 and post element 14 and includes parallel transversely extending side walls 21 and 22 and symmetrical end walls 23 and 24. For guiding purposes, the end walls are each formed of three downwardly tapered sections 23a, 23b and 23c and 24a, 24b and 24c. Each chamber 18 also has an open top end 31 (formed in cover 16), a bottom surface 32 and a central post 34, the latter two elements formed in post element 14. As best seen in FIGS. 2, 5 and 6, posts 34 are integrally and alternatingly formed with V-shaped support walls 36 intended to matingly fit into recesses 37 under transverse walls 30 of cover member 16. As best seen in FIGS. 3, 4, 7 and 8, adjacent clip chambers 18 are separated by narrow top walls 30 which extend transversely across the width of cover 16. The end clip chambers 18a obviously do not have a wall 30 on one side but are bounded by wall portions 38 and 39 of cover 16, as the case may be. Since all clip chambers are identical, only one will be described in detail.

The side walls 21 and 22 of each chamber 18 are formed of facing transverse top wall surfaces 40 and 50, respectively, associated with cover 16 and oppositely facing surfaces of transverse bottom wall members 60a, 60b associated with post element 14. Surface 40 faces inwardly into one clip chamber 18 and toward the left as seen in FIG. 2, and opposing surface 50 faces inwardly and to the right into the same chamber. The wall surfaces 40 and 50 are each formed by two contiguous wall surfaces 42, 44 and 52, 54, respectively, separated by V-shaped recess 37. Wall surfaces 40 and 50 may be tapered slightly inwardly as best seen in FIGS. 3 and 7. Integrally molded into the bottom ends of each wall surface 42, 44 and 52, 54 are downwardly directed resilient flaps 46, 48 and 56, 58. In the preferred embodiment, the space 59 between oppositely facing resilient flap pairs 46/56 and 48/58 is empty as best seen in FIGS. 3 and 7. Transverse bottom wall members 60a and 60b on either lateral side of support members 36 further define the bottom of side walls 21 and 22 of each clip chamber 18. Each member 60a(60b) has a wall surface 62(63), facing left in FIG. 2, and a wall surface 64(65), facing right in FIG. 2. The dimensions of facing flap pairs 46/56 and 48/58 and the top of bottom wall members 60b and 60a are such that vertical gaps 66 and 68, respectively, will be formed between these components.

In the embodiment shown, each post 34 has a planar side 70 and a non-planar side 72, the latter comprising a vertical portion 73 and an inclined portion 74 connecting the top end of the vertical portion to the top of post 34. The tip 76 of the post member 34 is rounded to a suitable degree which is not critical but which should be of a small enough radius of curvature not to interfere with free movement of clip 20 about the post while not being sharp enough to adversely affect the material from which the clip is made. Both sides of post 34 could be symmetrical but the non-symmetrical embodiment shown, with the planar side being aligned along the longitudinal centerline of the cartridge, has been found advantageous for the particular clip shown.

As best seen in FIGS. 3 and 4, clip 20 rests on the post 34 within each clip chamber 18. The tip 76 of the post rests on the inner side of the hinge of the clip and, in view of the non-symmetrical nature of clip 20, the clip is free to balance itself on post 34. While clip 20 is free to rock about post 34 somewhat, its motion is limited by contact with opposing flap pairs 46/56 and 48/58. While in the preferred embodiment the clip is provided with laterally extending bosses 80 and 82, these bosses are intended to lie under the bottommost ends of flap pairs 46/56 and 48/58 (as best seen in FIG. 3) and the interaction of the ends of the flaps with the bosses is not essential to retain the clip within its chamber. The opposing flaps 46/56 and 48/58 are molded in such a way that the normal unbiased gaps 90 and 92 between the flaps of each pair (best seen in FIGS. 7 and 8) is slightly smaller than the width of each clip body such that a slight compressive tension is maintained on the body of the clip when it is inserted into the chamber.

In actual use of the cartridge, the large top opening 31 of each chamber 18 and the successive tapering created by downwardly increasing tapered opposing surface pairs 23a/24a, 23b/24b and 23c/24c facilitates insertion of a clip applier jaw into the chamber and guides the jaws into secure engagement with the clip as the jaws become fully inserted. It will be noted that jaws 22a are wider than the clip body such that the resilient flaps are pushed downwardly by the jaws to enable the bosses 80 and 82 to be engaged by corresponding recess pairs 84 and 86 of the appliers.

Referring now to FIGS. 9-11, there is shown a cartridge 10' which is an alternate embodiment of the invention. The primary difference between cartridge 10' and cartridge 10 is that the former is integrally molded and does not include a cover element.

Cartridge 10' includes a base portion 112 and a body portion 114 integrally formed with the base portion 112 in such a way as to form parallel longitudinally extending channels 115 and 116. Extending upwardly from the floor 120 of body 114 are a plurality of longitudinally spaced transverse wall members 122 which intersect with a longitudinally aligned center post element 130. Post element 130 has a plurality of spaced center posts 132 which are aligned along the center of the chamber 134 created by adjacent wall members 122. These post members 132 support clips 133 and serve the same function and have the same shape as center posts 34 of the previous embodiment. Each wall member 122 has integrally formed therein a pair of downwardly and inwardly extending resilient flaps 140 and 142, it being understood that each chamber will have a pair of flaps 140 and 142 facing inwardly and serving the same purpose as resilient flap pairs 46/56 of the previous embodiment. It will also be understood that a symmetrical pair of resilient flaps is formed on each side of central post element 130.

It will be understood by those skilled in the art that numerous other modifications and improvements may be made to the preferred embodiment of the invention disclosed herein without departing from the spirit and scope thereof.

What is claimed is:

1. A cartridge for holding hemostatic clips comprising:
   an elongated body forming a plurality of longitudinally spaced chambers, each chamber for receiving a hemostatic clip and comprising:
   a central post for supporting an open hemostatic clip,
   a pair of facing transverse walls extending across said body, each said transverse wall having a downwardly extending transverse wall surface and an integrally formed resilient flap downwardly and inwardly extending from said wall surface towards the longitudinal central plane of said chamber, the bottommost end of said wall surfaces adapted to contact a hemostatic clip.

2. A cartridge for holding hemostatic clips comprising:
   a base portion;
   a cover portion having a plurality of clip receiving channels provided therein, said cover portion having a top surface and a pair of parallel side walls depending therefrom, said side walls adapted to mate with a portion of said base portion;
   an intermediate body portion adapted to be interposed between said base portion and said cover portion, said intermediate body portion comprising a plurality of generally triangular support sections each associated with a respective one of said clip chambers of said body portion, said triangular support sections adapted to extend into a portion of said cover portion and producing therewith a clip retaining chamber;
   a pair of opposed resilient fingers extending inwardly and downwardly into said clip chamber on either side of said triangular support section, said opposed fingers adapted to retain therebetween a hemostatic clip.

* * * * *